United States Patent [19]

Alvarez de Toledo

[11] Patent Number: 5,111,829

[45] Date of Patent: May 12, 1992

[54] STEERABLE HIGHLY ELONGATED GUIDEWIRE

[75] Inventor: Fernando Alvarez de Toledo, Concord, Mass.

[73] Assignee: Boston Scientific Corporation, Watertown, Mass.

[21] Appl. No.: 644,671

[22] Filed: Jan. 18, 1991

Related U.S. Application Data

[63] Continuation of Ser. No. 374,348, Jun. 28, 1989, abandoned.

[51] Int. Cl.⁵ .............................................. A61B 5/00
[52] U.S. Cl. ...................................... 128/772; 128/657
[58] Field of Search .................. 128/657, 772; 604/164, 604/170, 280, 281, 282

[56] References Cited

U.S. PATENT DOCUMENTS

| | | | |
|---|---|---|---|
| 2,118,631 | 4/1935 | Wappler | 128/349 |
| 2,463,149 | 11/1947 | Caine | 128/349 |
| 3,467,101 | 9/1965 | Fogarty et al. | 128/348 |
| 3,552,384 | 7/1967 | Pierie et al. | 128/303 |
| 3,704,711 | 12/1972 | Park et al. | 128/305 |
| 3,757,768 | 9/1973 | Kline | 128/DIG. 9 |
| 3,789,841 | 2/1974 | Antoshkiw | 128/772 |
| 3,867,945 | 2/1975 | Long | 128/349 |
| 3,890,977 | 6/1975 | Wilson | 128/418 |
| 3,906,938 | 9/1975 | Fleischhacker | 128/772 |
| 3,973,556 | 8/1976 | Fleischhacker et al. | 128/772 |
| 4,003,369 | 1/1977 | Heilman et al. | 128/772 |
| 4,019,925 | 4/1977 | Nenno et al. | 148/2 |
| 4,020,829 | 5/1977 | Willson et al. | 128/772 |
| 4,068,660 | 1/1978 | Beck | 128/DIG. 16 |
| 4,307,722 | 12/1981 | Evans | 128/344 |
| 4,351,341 | 9/1982 | Goldberg et al. | 128/348 |
| 4,388,076 | 1/1983 | Waters | 604/165 |
| 4,411,655 | 5/1983 | Schreck | 604/165 |
| 4,534,363 | 8/1985 | Gold | 128/772 |
| 4,545,390 | 10/1985 | Leary | 128/772 |
| 4,554,929 | 11/1985 | Samson et al. | 128/772 |
| 4,582,181 | 4/1986 | Samson | 128/348 |
| 4,586,969 | 5/1986 | Tamura et al. | 148/402 |
| 4,616,653 | 10/1986 | Samson et al. | 128/344 |
| 4,619,274 | 10/1986 | Morrison | 128/772 |
| 4,638,622 | 9/1986 | Samson et al. | 128/772 |
| 4,641,654 | 2/1987 | Samson et al. | 128/344 |
| 4,665,906 | 5/1987 | Jervis | 128/92 |
| 4,715,378 | 12/1987 | Pope, Jr. et al. | 128/344 |
| 4,719,924 | 1/1988 | Crittenden et al. | 128/772 |
| 4,721,117 | 1/1988 | Mar et al. | 128/772 |
| 4,748,986 | 6/1988 | Morrison et al. | 128/772 |

FOREIGN PATENT DOCUMENTS

| | | |
|---|---|---|
| 0141006 | 5/1983 | European Pat. Off. . |
| 0255234 | 2/1988 | European Pat. Off. . |
| 0274130 | 7/1988 | European Pat. Off. . |
| 0274412 | 7/1988 | European Pat. Off. . |
| 0279959 | 8/1988 | European Pat. Off. . |
| WO87/05792 | 10/1987 | PCT Int'l Appl. . |
| WO88/00810 | 2/1988 | PCT Int'l Appl. . |
| WO88/00844 | 2/1988 | PCT Int'l Appl. . |
| 2180454 | 4/1987 | United Kingdom ................ 604/280 |

OTHER PUBLICATIONS

Cope, "A New One-Catheter Torque-Guide System for Percutaneous Explorator Abdominal Angiography," Radiology, 92: 174–175 (1969).

Schetky, "Shape Memory Alloys" Kirk-Othmer Encyc. Chem. Tech. 20: 726–736.

Primary Examiner—Randy C. Shay
Attorney, Agent, or Firm—Fish & Richardson

[57] ABSTRACT

A steerable quidewire of length in excess of the order of about 350 centimeters and sufficient for use for gastrointestinal procedures includes an elongated body of flexible, kink-resistant material, the body having distal and proximal ends; a flexible distal tip formed of radiopaque material, fixedly jointed to the distal end of the body portion; and an elongated handle fixedly joined to the proximal end of the body. The handle, body and distal tip are formed of material and joined in a manner to transmit substantially all of an angular rotational force applied to the handle outside of a body to the distal tip within the body.

6 Claims, 2 Drawing Sheets

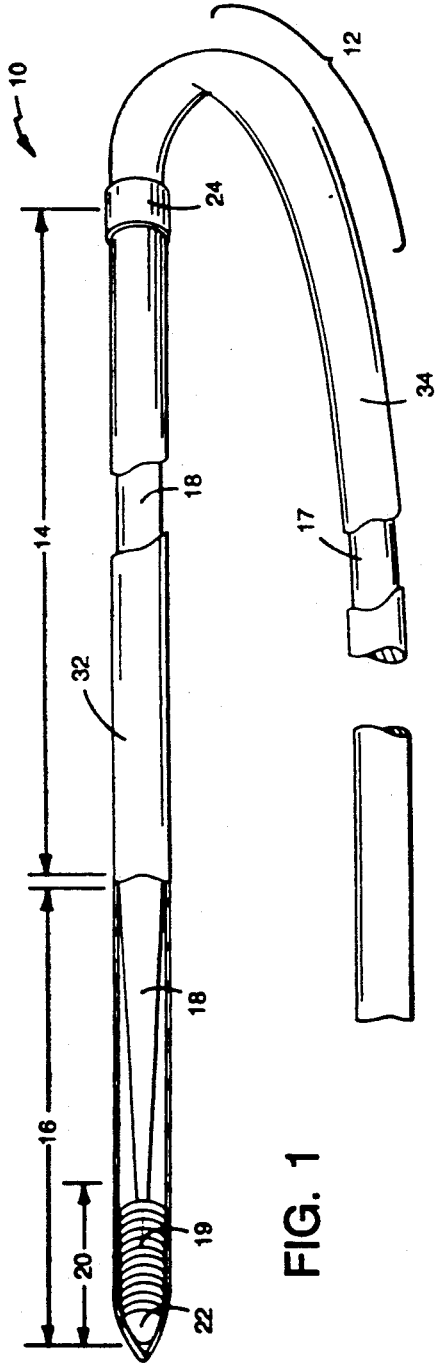
FIG. 1
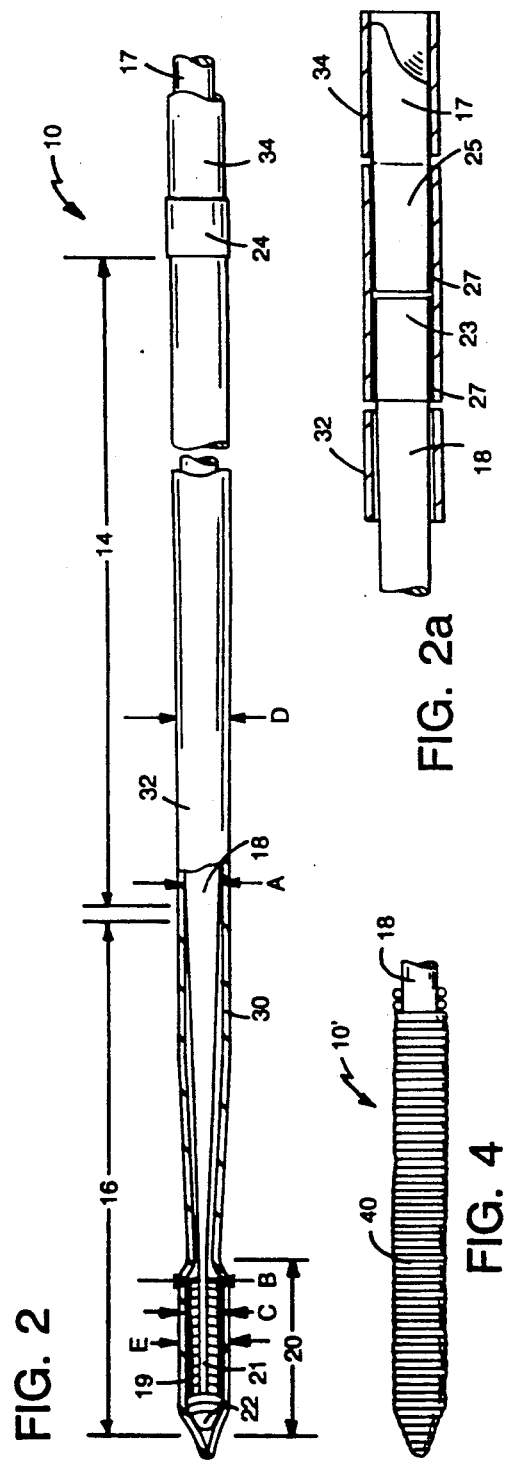
FIG. 2
FIG. 2a
FIG. 4

STEERABLE HIGHLY ELONGATED GUIDEWIRE

This application is a continuation of application Ser. No. 07/374,348, filed June 28, 1989, now abandoned.

BACKGROUND OF THE INVENTION

This invention relates to medical devices formed from elongated wires and coils used as guidewires, e.g., for navigating narrow passageways of a body.

Generally, the distal end of a guidewire is introduced into a body by a physician, e.g., through a puncture opening, and its progress is observed by a radioscope. The physician manipulates the tip of the guidewire through tortuous aspects of the body passageways to a site to be treated. A catheter or other medical device is advanced over the guidewire to the treatment site and the guidewire is then removed, leaving the catheter in place.

In order for the physician to have a maximum degree of control over the guidewire, and to ensure the patient's safety, it is important that the guidewire be as small in diameter as possible, particularly in the tip region, but not so small as to create a danger of the tip breaking loose in the body. It is also important that the guidewire be smooth to allow ready advancement and retraction within the passageways; that the distal tip of the guidewire be highly flexible to permit negotiation of difficult turns within the body; that the distal tip be visible by radioscope; that the guidewire be stiff enough axially to be advanced by pressure from the proximal end outside the body without kinking, i.e., turning back upon itself; and that the guidewire have good steerability or torque response, i.e., the tip to-handle turn ratio should be as close to 1:1 as possible, without whipping. Most prior art guidewires compromise these desired features, e.g., trading tip flexibility for good torque response.

Fuji Terumo Co. Ltd., EP 0 141 006 describes a guidewire having a rigid body portion, a flexible distal end portion, and a tapered portion in between the body and distal portions. At least portions of the body and/or distal end are formed of a super elastic metal member, e.g., a NiTi alloy (Nitinol). A coating, e.g., an elastomer, containing a radiopaque material, e.g., barium, is disposed over the length of the guidewire so that the position of the guidewire in a blood vessel can be determined. This coating is fixed to the distal end portion so that the guidewire may be flexibly deformed within the coating.

Samson U.S. Pat. No. 4.538,622 describes a guidewire having a proximal portion formed of stainless steel wire secured at its distal end to a first coil formed of stainless steel, which in turn is secured at its distal end to a second coil formed of a radiopaque material, e.g., platinum. The distal end of the second coil terminates in a rounded tip.

Leary U.S. Pat. No. 4,545,390 describes a guidewire having a main wire or rod formed of a material that may have a high degree of radiopacity and which tapers evenly at its distal end. A coil made of a radiopaque material, e.g., a platinum/tungsten alloy, fitted over the tapered portion extends slightly beyond the distal end of the main wire or rod, and terminates in a ball weld.

SUMMARY OF THE INVENTION

Generally, the invention features a gastro-intestinal guidewire, and a method for its use. According to the invention, a steerable guidewire of length in excess of the order of about 350 centimeters, and preferably at least about 450 centimeters, and sufficient for use for gastro-intestinal procedures comprises an elongated body portion of flexible, kink resistant material, the body portion having a distal end and a proximal end, a flexible distal tip portion fixedly joined to the distal end of the body portion, the distal tip portion formed of radiopaque material, an elongated handle portion fixedly joined to the proximal end of the body portion, the handle portion, body portion and distal tip portion being formed of material and joined in a manner to transmit substantially all of an angular rotational force applied to the handle portion outside of a body to the distal tip portion within the body.

In preferred embodiments, the ratio of angular rotational force applied to the handle to angular rotation of the distal tip portion is of the order of about 1:1; the body portion is formed of super elastic material, e.g., Nitinol; the radiopaque material is platinum; the body portion is joined at its distal end to the tip portion by a ball weld; the guidewire further comprises a coupling sleeve disposed about a joint between adjacent portions of the guidewire, e.g., the body portion and the elongated handle portion, the coupling sleeve comprising a crimped joint, a glued joint or a spot welded joint; and a plastic sleeve, e.g. of heat shrinkable, polyamide or other material, and/or a wire coil may be disposed over the tip and body portions.

The invention further includes a method for using the guidewire of the invention.

A guidewire of this invention has the following advantages: the use of a super elastic material, such as Nitinol wire, in the body portion in conjunction with a radiopaque tip portion provides a guidewire which is flexible, kink-resistant, and visible with a radioscope; when the body portion of the guidewire is advanced through a passageway, it is curved and restored without plastic deformation, making it easier to accommodate tortuous routes to a treatment site; and the body portion is elastic and presses against passageway walls without recoiling out of the passageway, and thus holds the distal portion in place and facilitates advancement of a catheter.

Still other advantages include the following. The guidewire is sufficiently small in diameter and sufficiently long for gastro intestinal use; the ball weld joint provides the necessary strength between the tip and body portions so that the platinum coil does not break away from the Nitinol wire; the sleeve provides sufficient smoothness to allow the guidewire to be advanced and retracted readily; the sleeve also aids in torque transmission from proximal to distal ends of the guidewire; the platinum coil tip is radiopaque as well as flexible; and the handle portion provides the necessary stiffness to advance and retract the guidewire without kinking, and sufficient torque to turn the guidewire without whipping.

These and other features and advantages will be seen from the following description of a presently preferred embodiment, and from the claims.

DESCRIPTION OF THE PREFERRED EMBODIMENT

We first briefly describe the drawings.

DRAWINGS

FIG. 1 is a generally schematic view, partially in section, of a guidewire of the invention;

FIG. 2 is a longitudinal view of the distal end of the guidewire partially in section;

FIG. 2A is a similar view of the joint region between adjacent portions of the guidewire, specifically between body and handle;

FIG. 4 is a schematic view of the distal portion of an alternate embodiment of the guidewire of the invention.

STRUCTURE

Figure 3:
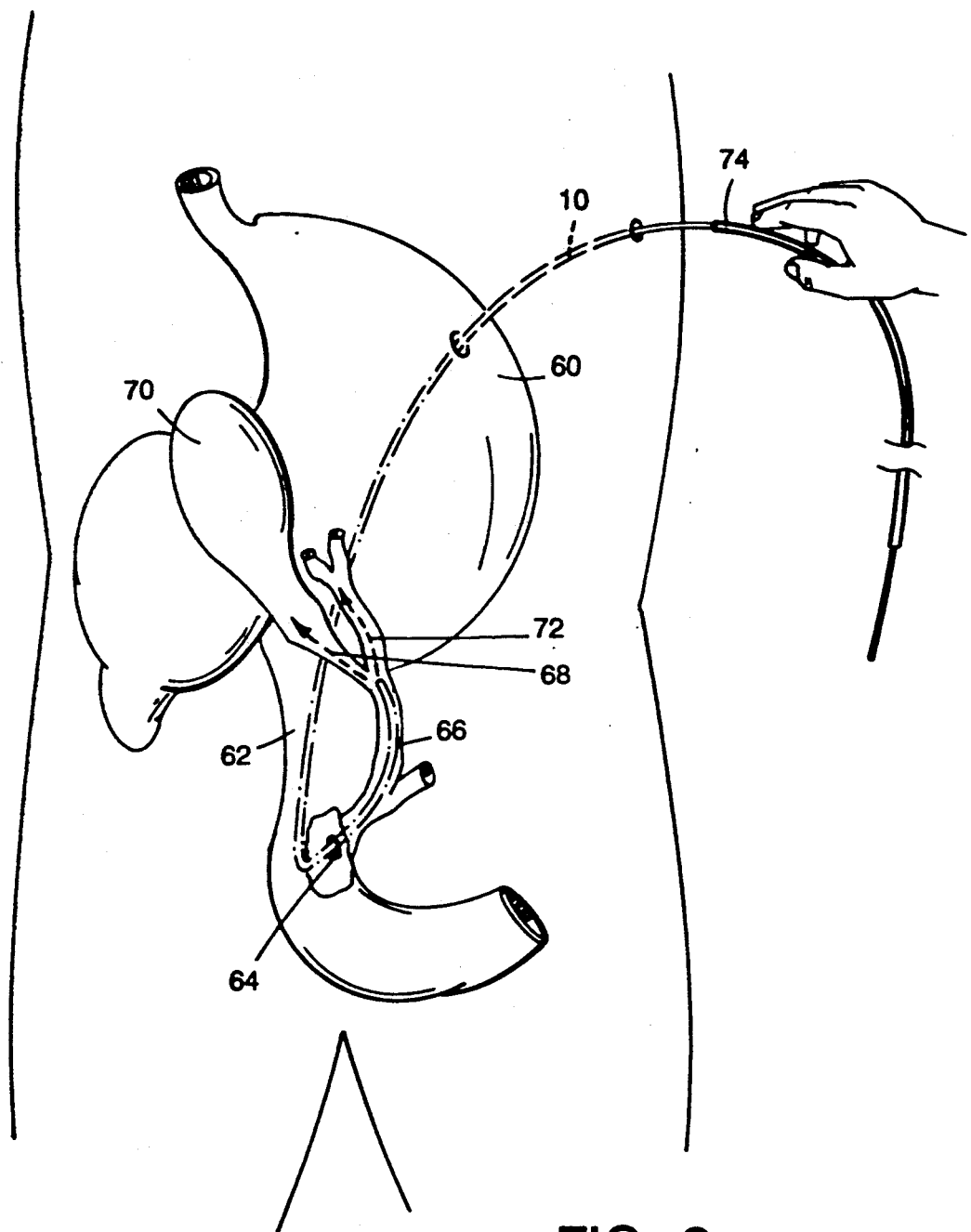
FIG. 3 is a schematic view showing a guidewire of the invention employed in the gastro-intestinal region of a human body.

Referring to FIGS. 1 and 2, guidewire 10, approximately 450 cm in length, has a handle portion 12 (approximately 400 cm in length), a body portion 14 (approximately 40 cm in length), and a distal portion 16 (approximately 10 cm in length), including a distal tip region 20 (approximately 3 to 5 cm in length). The guidewire terminates distally in a rounded ball tip element 22. The total length of guidewire 10 makes it suitable for use in the gastro-intestinal region of the body. A guidewire of this length is also useful as an exchange wire because when it is inserted into a body and advanced through a passageway an equal or greater length of guidewire 10 remains outside the body to allow a second device, e.g., a catheter (74, FIG. 3), to be advanced over the guidewire.

Handle portion 12 is formed of stainless steel wire 17, which provides sufficient stiffness to allow the physician to push guidewire 10 through a passageway and also to prevent its recoil from the body passage. Body portion 14 is a solid wire 18 formed of super elastic, flexible, and kink-resistant material, for example, a nickel titanium system commonly referred to as NITINOL (an acronym for "Nickel-Titanium Naval Ordinance"). Other alloys exhibiting the desired properties include, e.g., Silver Cadmium (Ag-Cd), Gold-Cadmium (Au-Cd), Gold-Copper-Zinc (Au-Cu Zn), Copper-Aluminum-Nickel (Cu-Al Ni), Copper-Gold Zinc (Cu-Au Zn), Copper-Zinc (Cu-Zn), Copper-Zinc Aluminum (Cu Zn-Al), Copper-Zinc-Tin (Cu-Zn-Sn), Copper-Zinc-Xenon (Cu-Zn-Xe), Iron Beryllium ($Fe_3Be$), Iron Platinum ($Fe_3Pt$), Indium Thallium (In-Tl) and Titanium Nickel (Ti-Ni) (Schetsky, L. McDonald, "Shape Memory Alloys", *Encyclopedia of Chemical Technology* (3rd ed.), John Wiley & Sons, 1982, vol. 20, pp. 726-736); also Nickel-Titanium-Vandium (Ni Ti-V), Copper Tin (Cu Sn) and Iron-Nickel-Titanium Cobalt (Fe Ni-Ti Co). Tip portion 16 is a tapered continuation of the Nitinol wire 18 of body portion 14 and has mounted about its distal extremity, in distal tip region 20, a radiopaque, flexible platinum coil 19, which allows the guidewire to make a 90° turn in a passageway of ⅛ to ¼ inch radius without breakage or permanent deformation of the tip.

Platinum coil 19 is fitted over the distal end portion 21 of Nitinol wire 18 and joined to guidewire 10 only at its distal end to the ball weld tip 22, as described below; the proximal portion of the coil 19 floating freely about the distal tapered portion 21 of the body portion. The proximal end of Nitinol wire 18 is joined to the distal end of stainless steel wire 17 at joint 24. Referring to FIG. 2A, the proximal end 23 of wire 18 and distal end 25 of wire 17 extend into coupling sleeve 24 and are joined together therein, e.g., by crimping of the sleeve as shown in FIG. 2, or by spot welding or adhesive, e.g., cyanoacrylate (27, FIG. 2A).

Sleeve 32, 34 formed of a suitable material, e.g. a shrink sleeve of polytetrafluoroethylene (PTFE) or polyethylene or a sleeve of polyamide material or other suitable plastic material, is disposed over body and tip portions 14, 16, and over handle portion 12.

Body portion 14 of guidewire 10 is formed of solid Nitinol wire 18 normally equal in diameter at its proximal end to the diameter of stainless steel wire 17, and generally having an outer diameter, A, e.g., 0.023 inch. The distal portion of Nitinol wire 18 in the distal tip region 20 is tapered, reaching an outer diameter B, e.g., 0.007 to 0.012 inch and preferably 0.010 inch, in the distal tip region 20, about 3 to 5 cms in length. Platinum coil 19 of tip portion 16, having an outer diameter, C, e.g., 0.018 inch, and an inner diameter approximately that of the outer diameter of the Nitinol wire in region 20, i.e., diameter B, is fitted over the wire in region 20 and ball welded to the Nitinol wire 18 at the distal tip 22. Sleeves 32, 34 have thickness of about 0.005 to 0.006 inch, increasing the diameter of body portion 14 to D, e.g., 0.035 inch. The coupling sleeve 24 lies between the opposed ends of sleeves 32, 34 and preferably is not covered. The diameter of tip portion 16 is increased to an outer diameter E, e.g., 0.028 inch, where the sleeve 32 covers the distal coil 19, then tapers distally over the rounded tip 22.

MANUFACTURE

Platinum coil 19 of distal tip region 20 is a single or multifilar coil of flat or round wire, and can be tweeked, i.e., the individual coils can be spaced apart, to make tip portion 20 more flexible. Platinum coil 19 is fitted over necked down region 21 and ball welded to the distal end of Nitinol wire 18 at distal tip 22. Parameters for the ball welding include, e.g., using tungsten inert gas to plasma arc weld tip 22 using a chill clamp fixture, a weld current of less than 1.25 amps, and a weld time of 0.08 seconds. Stainless steel wire 17 of handle portion 12 is then crimped, spot welded or glued to the proximal end 23 of Nitinol wire 18 of body portion 14 using coupling sleeve 24, and sleeves 32, 34 disposed over tip and body portions 16 and 14 by standard procedure.

Use

Referring to FIG. 3, guidewire 10 can be used for treatment of gastro-intestinal ailments. Generally, a physician inserts the distal end, i.e., rounded tip 22, of guidewire 10 into a body. Axial pressure is applied to the proximal portion, i.e., handle 14, of guidewire 10 to advance or retract guidewire 10. The rounded tip 22 of guidewire 10 is steered by rotating handle 14 to direct rounded tip 22 to various passageways. In the figure, guidewire 10 is shown inserted through a puncture opening in a stomach 60, and advanced through a duodenum 62, to a duodenal papilla 64, and into a bile duct 66 at which point the physician can direct rounded tip 22 of guidewire 10 through a cystic duct, as shown by arrow 68, to a gallbladder 70, or into a hepatic duct, as shown by arrow 72. A catheter 74 can then be advanced over guidewire 10, and guidewire 10 removed when catheter 74 is in place.

Other embodiments are within the following claims. For example, a wire coil 40 may be disposed over the tip and body portions of a guidewire 10' (FIG. 4). A sleeve as described above may be further disposed thereabout.

I claim:

1. A steerable guidewire of length in excess of the order of about 350 centimeters and sufficient for use in gastro-intestinal procedures, said guidewire comprising an elongated distal body portion having a distal end and a proximal end, an elongated handle portion extending proximally of the proximal end of said distal body portion, at least a distal end region of said distal body portion, including said distal end, being formed of a flexible kink resistant material comprising a super-elastic metallic nickel-titanium alloy material, a flexible distal tip portion ball welded to said distal end of said elongated distal body portion, said distal tip portion being formed of a radiopaque material comprising platinum, and a plastic sleeve disposed closely about said distal end region of said distal body portion and said distal tip portion joined thereto, said guidewire constructed in a manner whereby substantially all of an angular rotational force applied to said handle portion outside of a patient's body is transmitted to the distal tip portion within the body.

2. The steerable guidewire of claim 1 wherein the ratio of angular rotation force applied to the handle to angular rotation of the distal tip portion is of the order of about 1:1.

3. The steerable guidewire of claim 1 wherein said plastic sleeve is formed of heat shrinkable material.

4. The steerable guidewire of claim 1 wherein said plastic sleeve is formed of polyamide material.

5. The steerable guidewire of claim 1 comprising a wire coil disposed over said body portion and said tip portion.

6. The steerable guidewire of claim 1 wherein the length of said guidewire is of the order of about 450 centimeters.

* * * * *

UNITED STATES PATENT AND TRADEMARK OFFICE
CERTIFICATE OF CORRECTION

PATENT NO.   :  5,111,829

DATED        :  May 12, 1992

INVENTOR(S)  :  Fernando Alvarez de Toledo

It is certified that error appears in the above-identified patent and that said Letters Patent is hereby corrected as shown below:

On the title page: Item [56]:

In the References Cited:

Subheading U.S. PATENT DOCUMENTS, "4,638,622  9/1986" should be --4,538,622  9/1985--.

In the Abstract:

Line 1, "quidewire" should be --guidewire--.

Signed and Sealed this

Tenth Day of August, 1993

Attest:

MICHAEL K. KIRK

*Attesting Officer*     *Acting Commissioner of Patents and Trademarks*